United States Patent
Garlick et al.

(10) Patent No.: US 7,259,897 B2
(45) Date of Patent: Aug. 21, 2007

(54) SYSTEM, METHOD AND APPARATUS FOR DIRECT IMAGING IN ULTRASONIC HOLOGRAPHY

(75) Inventors: George F. Garlick, Richland, WA (US); Todd F. Garlick, Pasco, WA (US)

(73) Assignee: Holographic Engineering LLC, Richland, WA (US)

( * ) Notice: Subject to any disclaimer, the term of this patent is extended or adjusted under 35 U.S.C. 154(b) by 0 days.

(21) Appl. No.: 11/274,050

(22) Filed: Nov. 15, 2005

(65) Prior Publication Data

US 2006/0232842 A1    Oct. 19, 2006

Related U.S. Application Data

(60) Provisional application No. 60/628,140, filed on Nov. 15, 2004.

(51) Int. Cl.
*G03H 1/00* (2006.01)
(52) U.S. Cl. .............. 359/1; 367/7; 367/8; 367/10; 73/603; 73/605; 359/901
(58) Field of Classification Search ............... 359/1, 359/901; 367/7–8, 10; 73/603, 605
See application file for complete search history.

(56) References Cited

U.S. PATENT DOCUMENTS

| 3,879,989 A | * | 4/1975 | Brenden | .............. 73/605 |
| 3,964,052 A |   | 6/1976 | Langlois | ............ 340/5 H |
| 5,212,571 A |   | 5/1993 | Garlick et al. | |
| 5,235,553 A |   | 8/1993 | Garlick et al. | |
| 5,329,202 A |   | 7/1994 | Garlick et al. | |
| 6,353,576 B1 | * | 3/2002 | Garlick et al. | ............ 367/10 |

* cited by examiner

*Primary Examiner*—Leonidas Boutsikaris
(74) *Attorney, Agent, or Firm*—Seed IP Law Group PLLC

(57) ABSTRACT

An acoustical holographic imaging method and apparatus for introducing a reference wave into a hologram surface such that the reference wave does not interfere with an object placed adjacent to or in close proximity to the hologram surface. More particularly, the ultrasonic holographic imaging system may use a reference wave introduced on the side of a thin (3 element) detector that acts as a wave guide; to introduce the reference wave to a liquid-to-gas interface or alternatively, from the topside of the detecting surface through a liquid-to-liquid interface. The system eliminates the acoustic lens system, thereby reducing the size and cost of the system. Further, an object may be placed at the detecting surface, increasing the depth of field of the resultant image and reducing the energy needed from the object source. The system may additionally utilize multiple reference sources.

23 Claims, 6 Drawing Sheets

SYSTEM, METHOD AND APPARATUS FOR DIRECT IMAGING IN ULTRASONIC HOLOGRAPHY

BACKGROUND OF THE INVENTION

1. Field of the Invention

The present invention is directed generally to acoustic imaging and more particularly the direct imaging of an object utilizing the method of acoustical holography whereby the object being imaged can be in close proximity to the hologram surface.

2. Description of the Related Art

Holography involves combining or interfering an object wave or energy with a reference wave or energy to form an interference pattern referred to as the hologram. A fundamental requirement for the forming of the hologram and the practice of holography is that the initial sources of the object wave and reference wave or energy are coherent with respect to the other wave. That is to say that all parts of both the object wave and the reference wave are of the same frequency and of a defined orientation, namely, a fixed spatial position and angle between the direction of propagation of the two sources. When performing holography the object wave is modified by interference with the structure within the object of interest. As this object wave interacts with all points of the object in the path of the wave, the three-dimensional features of the object impart identifying phase and amplitude changes on the object wave. Since the reference wave is an unperturbed (pure) coherent wave, its interference with the object wave results in an interference pattern that identifies the 3-D positioning and characteristics (ultrasonic absorption, diffraction, reflection, and refraction) of the scattering points of the object.

A second process, (the reconstruction of the hologram) is then performed when a coherent viewing source (usually light from a laser) is transmitted through or reflected from the hologram. The hologram pattern diffracts light from this coherent viewing or reconstruction source in a manner to faithfully represent the 3-D nature of the object, as seen by the ultrasonic object wave.

Thus, traditionally, to perform holography, coherent wave sources are required. This requirement currently limits practical applications of the practice of holography to the light domain (e.g., a laser light) or the domain of acoustics (sometimes referred to as ultrasound due to the practical application at ultrasonic frequencies) as these two sources are currently the only available coherent energy sources. Thus, further references to holography or imaging system will refer to the through-transmission holographic imaging process that uses acoustical energies usually in the ultrasonic frequency range and more specifically from 1 to 10 MHz. Alternatively, higher or lower frequencies would also apply.

In the practice of ultrasound holography, one key process is the generation of the ultrasound, such as by a large area coherent ultrasound transducer. A second key process is the projection of the object wave information from a specific volume within the object into the hologram detection plane by means of the ultrasonic lens projection system. A third key process is the detection and reconstruction of the ultrasonic hologram into visual or useful format.

Although other configurations can be utilized, a common requirement of the source transducers for both the object and reference waves is to produce a large area plane wave having constant amplitude across the wave front and having a constant frequency for a sufficient number of cycles to establish coherence. Such transducers will produce this desired wave if the amplitude of the ultrasound output decreases in a Gaussian distribution profile as the edge of the large area transducer is approached. This decreasing of amplitude as the edge is approached, reduces or eliminates the "edge effect" from the transducer edge, which would otherwise cause varying amplitude across the wave front as a function distance from the transducer.

In the process of through-transmission ultrasonic holographic imaging, the pulse from the object transducer progresses through the object, then through a focusing lens system and at the appropriate time, the pulse of ultrasound is generated from the reference transducer such that the object wave and reference wave arrive at the detector at the same time to create an interference pattern (i.e., the hologram). For broad applications, the transducers need to be able to operate at a spectrum or bandwidth of discrete frequencies. Multiple frequencies allow comparisons and integration of holograms taken at selected frequencies to provide an improved image of the subtle changes within the object.

A hologram can also be formed by directing the object wave through the object at different angles to the central axis of the lens system. This is provided by either positioning or rotating the object transducer around the central axis of the lens system by using multiple transducers positioned such that the path of transmission of the sound is at an angle with respect to the central axis of the lens system.

With a through-transmission imaging system, it is important to determine the amount of resolution in the "z" dimension that is desirable and achievable. Since the holographic process operates without limits of mechanical or electronic devices to detect and form the image, but rather reconstructs images from wave interactions, the resolution achievable can approach the theoretical limit of ½ the wavelength of the ultrasound used. However, the amount of information displayed for the user in this situation may be too great. It may be desirable to limit the "z" direction image volume so that on can "focus" in on one thin volume slice and thereby reduce the amount of data. Thus, it is of value to develop a means for projecting a planar slice within a volume into the detector plane. One such means is a large aperture ultrasonic lens system that will allow the imaging system to "focus" on a plane within the object. Additionally, this lens system and the corresponding motorized computer controlled lens drive will allow one to adjust the focal plane and at any given focal plane to be able to magnify or demagnify at a selected z dimension position (i.e., a zoom lens).

The image is detected and reconstructed at the detector. Standard photographic film may be used for the recording of light holograms and the 3-D image reconstructed by passing laser light through the film or reflecting it from the hologram pattern embossed on the surface of an optical reflective surface. However, there is no equivalent "film" material to record the intricate phase and amplitude pattern of a complex ultrasonic wave. One of the most common detectors uses a liquid-air surface or interface to record, in a dynamic way, the ultrasonic hologram formed. The sound energy at the frequency of ultrasound (above range of human hearing) will propagate with little attenuation through a liquid (such as water) but cannot sustain substantial propagation through air. At these higher frequencies (e.g., above 1 MHz) the ultrasound will not propagate through air because the wavelength of the sound energy is so short [$\lambda$(wavelength)=v (velocity)/f(frequency)]. The density of air (approximately 0.00116 $g/cm^3$) is not sufficient to couple these short wavelengths and allow them to propagate for any significant distance. On the other hand the density of a liquid (e.g., water) is a favorable media to couple and propagate such wavelengths. For example, the velocity of sound in air is approximately 346 meter/second whereas in water it is approximately 1497 meter/second. Thus, for water, both the density (1 g/cm$^3$) and the wavelength (~1.5 mm at 1 MHz) are significantly large that ultrasound can propagate with little attenuation. In contrast, for air both the density (0.00116 g/cm$^3$) and wavelength (0.346 mm at 1 MHz) are sufficiently small such that the energy at these ultrasonic frequencies will not propagate.

Thus, when ultrasound propagating in a liquid encounters a liquid-air interface the entire amount of the energy is reflected back into the liquid. Since ultrasound (or sound) propagates as a mechanical force it is apparent that the reflection (or changing direction of propagation) will impart a forward force on this liquid-air interface. This force, in turn, will distort the surface of the liquid. The amount of surface distortion will depend upon the amplitude of the ultrasound wave at each point being reflected and the surface tension of the liquid. Thus, the pattern of the deformation is the pattern of the phase and amplitude of the ultrasonic wave at the plane (i.e. the ultrasonic hologram).

In this manner, the liquid-air interface can be readily used to provide a near real-time recorder ("film equivalent") for an ultrasonic hologram. The shape of the surface deformation on this liquid-air detector is the representation of the phase and amplitude of the ultrasonic hologram formed by the interference of the object and reference ultrasonic waves.

The greatest value of the ultrasonic holographic process is achieved by reconstructing the hologram in a usable manner, usually in light, to make visible the structural nature of the initial object. In the case of a liquid-air interface, the reconstruction to achieve the visible image is accomplished by reflecting a coherent light from this liquid-air surface. This is the equivalent process to reflecting laser light from optically generated hologram that is embossed on the surface of a reflecting material (e.g., thin aluminum film).

The reflected light is diffracted (scattered) by the hologram to diffractive orders, each of which contains image information about the object. These diffracted orders are referred to as ±nth orders. That part of the reconstructing light that does not react with the hologram is referred to as zero order and is usually blocked so that the weaker diffracted orders can be imaged. The higher the diffracted order the greater is the separation angle between the zero order of reflected light. Once reconstructed, the image may be viewed directly, by means of a video camera or through post processing processes.

Ultrasonic holography is illustrated in prior art FIG. 1. FIG. 1 shows a plane wave of sound 12 (i.e., ultrasound) that is generated by a large area object transducer 10. One example of a large area object transducer is described in U.S. Pat. No. 5,329,202. The sound is scattered (i.e., diffracted) by structural points within the object. The scattered sound 14, from the internal object points that lie in the focal plane 16, are focused (i.e., projected) into a hologram detector plane 18 of a hologram detector 20. The focusing is accomplished by an ultrasonic lens system 22, which focuses the scattered sound into the hologram detector plane 18. According to U.S. Pat. No. 5,235,553, an ultrasonic lens is described that may be satisfactorily used for the ultrasonic lenses illustrated as the lens system 22 in FIG. 1. The ultrasonic lens system 22 also allows the imaging process to magnify the image (i.e., zoom) or change focus position. According to U.S. Pat. No. 5,212,571 a lens system is illustrated that can magnify the image and change focus position, and may be used satisfactorily for the lens system 22.

Since the focal point 24 of the unscattered sound is prior to the hologram detector plane 18, this portion of the total sound again expands to form the transparent image contribution (that portion of the sound that is transmitted through the object as if it were transparent or semi-transparent). In such an application an ultrasound reflector 26 is generally used to direct the object sound at a different angle thus impinging on the horizontal hologram detector plane 18; the hologram detector plane 18 usually contains a liquid 28 that is deformed by the ultrasound reflecting from the liquid-air interface.

When a reference wave 30 and the object wave are simultaneously reflected from the hologram detector plane 18, the deformation of the liquid-air interface is the exact pattern of the ultrasonic hologram formed by the object wave (12 combined with 14) and the "off-axis" reference wave 30.

This ultrasonic hologram formed on the detector plane 18 is subsequently reconstructed for viewing by using a coherent light source 32, which may be passed through an optical lens 34, and reflected from the holographic detector plane 18. A hologram detector suitable for use as the hologram detector 20 illustrated in FIG. 1 is described in U.S. patent application Ser. No. 09/589,863.

In the practice of ultrasonic holography an object wave is passed through or reflected from the interior or exterior structural characteristics of an object being investigated. Since this is off-axis holography, a reference wave is required to form the ultrasonic (or acoustical) hologram. Since the reference wave needs to pass unaltered from the reference transducers to the hologram area, the prior art systems required some volume or space on the ultrasonic side of the hologram that is free of the object, thus allowing an unaltered path for the reference.

These conditions required that there was some distance from the object to the hologram. This meant that the "object distance" was great; the object distance then determined the image distance. Thus, an opportunity to have a full 3-D (three dimensional) view is compromised since the aperture size to the object distance limits the 3-D information.

BRIEF SUMMARY OF THE INVENTION

The present invention provides a process and apparatus for volumetric holographic acoustical imaging that will allow a much smaller system footprint, with lower cost of production, than was possible under the prior art. Specifically, the process and apparatus provides an acoustical holographic imaging system that introduces the reference wave into the hologram surface in such a way as to not interfere with an object placed adjacent to or in close proximity to the hologram surface. Aspects of the invention further provide a process and apparatus that introduces the reference wave from the side of the holographic detecting surface. Further aspects of the invention provide an alternate process and apparatus that introduces the reference wave into the holographic detecting surface from the opposite side of the object. According to additional aspects, the process and apparatus further provides for an acoustical holographic imaging system utilizing multiple reference sources.

Aspects of the invention provide a process and apparatus for creating acoustical holographic images with greater depth of field on a much more portable system than prior art. According to one embodiment, the process and apparatus provides an ultrasonic holographic imaging system having the object to be inspected placed adjacent to the detector and yet still providing an off axis acoustic reference wave without direct interference with the object. For example, the process and apparatus provides an ultrasonic holographic imaging system having the reference wave introduced in a narrow, thin, configuration. This configuration acts as a "wave guide" and coupler of reference sound into the hologram at an "off-axis" angle, or alternatively, uses a reference wave introduced from the topside of the detecting surface utilizing a liquid-to-liquid interface; alternatively, the system may utilize a liquid-to-gas interface.

According to aspects described herein, the introduction of the reference eliminates the requirement for the acoustic lens system required by prior art, which thereby reduces the size and cost of the system. Another result of utilizing the inventive process is the ability to place the object at the detecting surface thereby increasing the depth of field of the resultant image and reducing the amount of energy required from the object source.

According to aspects of the invention, the object is placed adjacent to the bottom surface of the holographic detector. This bottom surface consists of a narrow fluid filled channel that acts as an acoustic waveguide for the reference wave. The object source is placed so that the object is between the object source transducer and the bottom surface of the detector. An acoustic signal passes through the object, and then through the bottom surface or reference wave-guide apparatus of the holographic detector, ultimately creating an "object pattern" on the holographic detecting surface. The reference source transducer generates an acoustic signal at the side of the detector at an oblique angle causing the acoustic wave to travel in a zigzag fashion down the detector floor element; thus, the detector floor element acts as a waveguide. The top surface of the detector floor element or waveguide is transmissive to ultrasound, thus allowing a portion of the reference source to interfere with the object pattern formed on the detecting surface, thus creating the desired hologram. In an alternate embodiment the reference source is placed in the volume above the detecting surface that is with a liquid or gas of appropriate characteristics. Appropriate characteristics include, for example, being transmissive to both ultrasound and light, and having an acoustic impedance difference from the detector imaging liquid so that there is a reflection of the reference wave at this interface.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale. Further, the particular shapes of the elements as drawn, are not intended to convey any information regarding the actual shape of the particular elements, and have been solely selected for ease of recognition in the drawings.

DETAILED DESCRIPTION OF THE INVENTION

In the following description, certain specific details are set forth in order to provide a thorough understanding of various embodiments of the invention. However, one skilled in the relevant art will recognize that the invention may be practiced without one or more of these specific details, or with other methods, components, materials, etc. In other instances, well-known structures associated with ultrasonic holography have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the claimed invention.

An acoustical holographic imaging method and apparatus for introducing a reference wave into a hologram surface such that the reference wave does not interfere with an object placed adjacent to or in close proximity to the hologram surface. More particularly, according to aspects of the present invention, the ultrasonic holographic imaging system may use a reference wave introduced from the topside of the detecting surface through a liquid-to-liquid interface; alternatively, the reference wave may be introduced through a liquid-to-gas interface. The system eliminates the acoustic lens system, thereby reducing the size and cost of the system. Further, an object may be placed near a detecting surface, increasing the depth of field of the resultant image and reducing the energy needed from the object source. Further, the system allows viewing of the three-dimensional (3-D) characteristics by optically reconstructing the image to allow focus on any slice within the 3-D image. The system may additionally utilize multiple reference sources.

Figure 2:
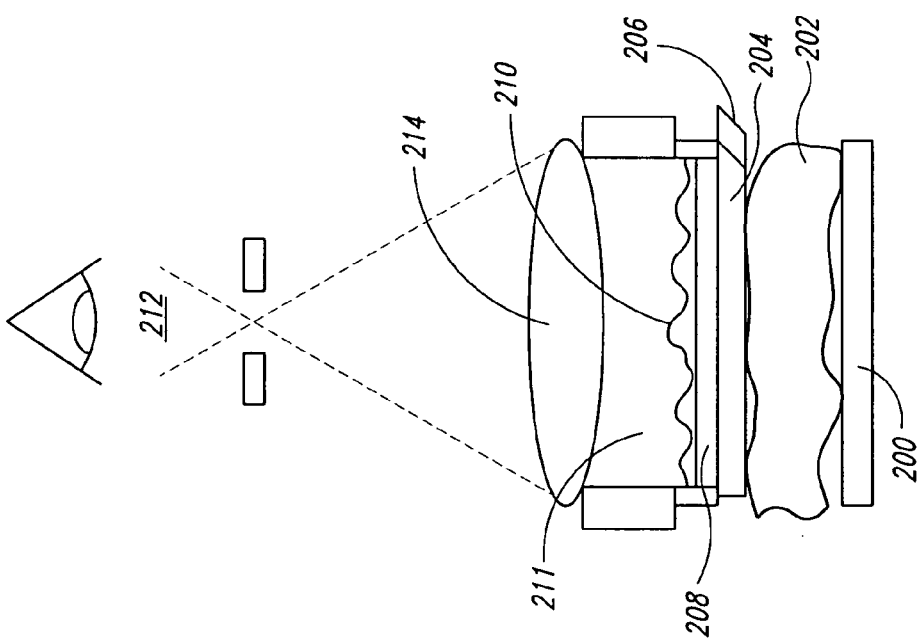
FIG. 2 is a pictographic representation of an acoustic holographic system wherein the reference wave is injected from the side in the ultrasonic holographic process according to principles of the present invention.

FIG. 2 is a pictographic representation of an acoustic holographic system wherein the reference wave is injected from the side in the ultrasonic holographic process according to principles of the present invention. FIG. 2 illustrates an object wave transducer 200 adjacent the object and a reference wave emmitter 206 introduced to allow the object 202 to be in close proximity to the hologram 210, thus eliminating the need for an ultrasonic lens and a large volume of sound coupling, for example, water. The configuration of the present system thus reduces size and cost of the system while increasing purity of the object wave in the hologram.

According to one aspect of the invention, FIG. 2 shows an orientation and coupling of the reference wave emitter 206 into the liquid surface hologram 210 to allow for a more compact footprint of an acoustic holographic system. An acoustical waveguide assembly 204 for the reference/hologram detector configuration replaces the need for the ultrasonic lens of the prior art. The acoustical waveguide assembly 204 is positioned against the floor 208 and is shown in greater detail in FIG. 4.

The optical reconstruction 212 shown in FIG. 2 is one exemplary configuration, it is understood that there are a number of optical reconstruction configurations that can be used with this system. Further, the top element 214 of FIG. 2 is shown in the form of a lens, however, in alternative optical reconstruction configurations this top element 214 may be an optical transparent element such as a piece of glass or may be open to the optical reconstruction element mounted above the detecting surface.

Figure 1:
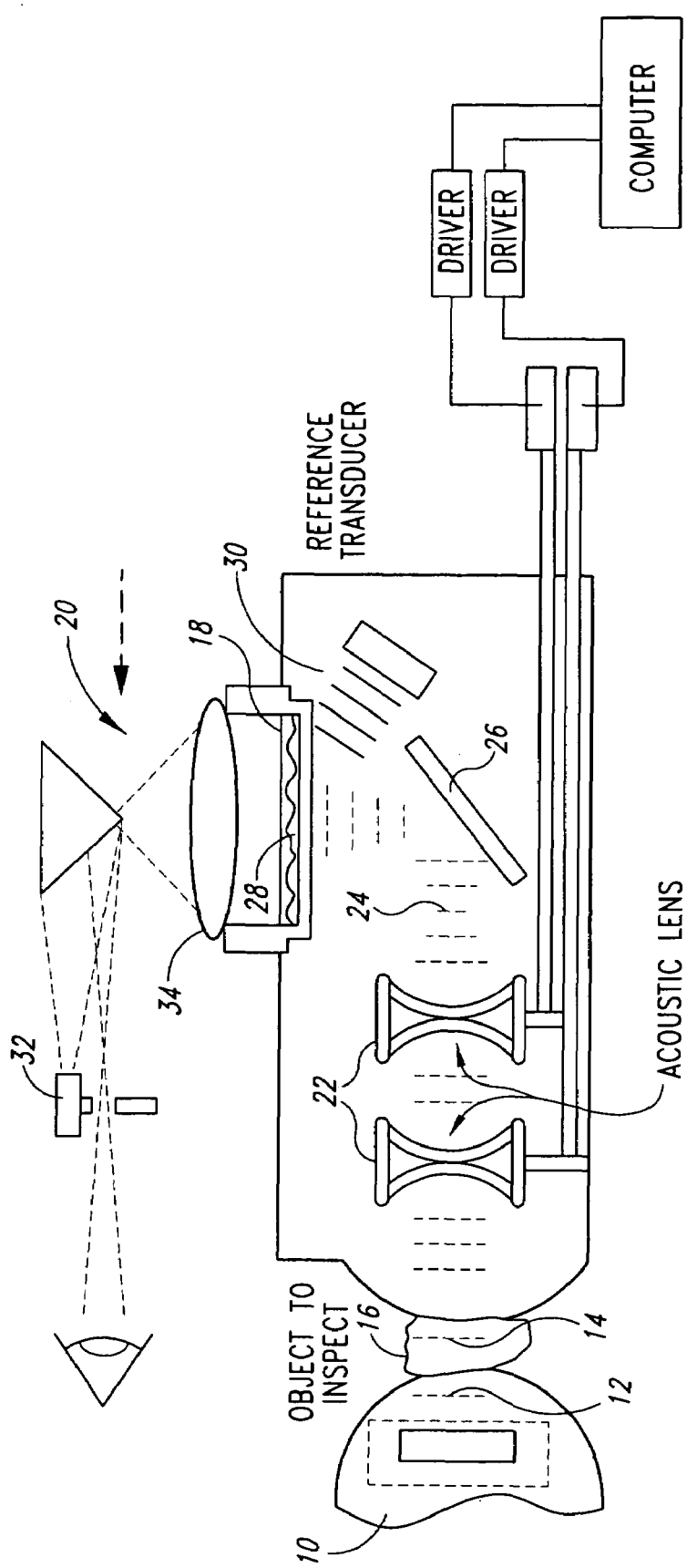
FIG. 1 is a pictographic representation of acoustical holography of an acoustic holographic system according to the prior art.
Figure 3:
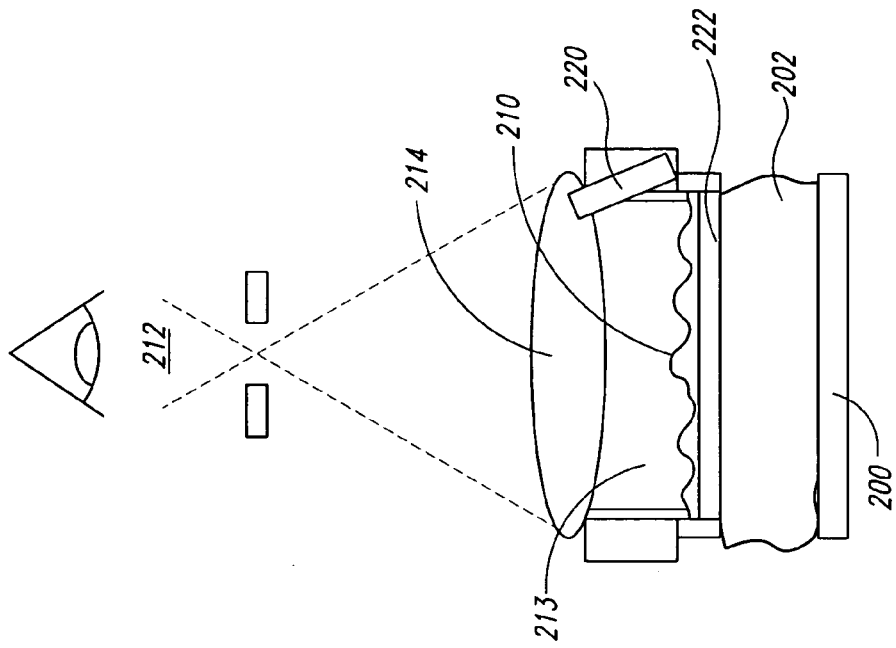
FIG. 3 is an alternative embodiment of a pictographic representation of the acoustic holographic system wherein the reference wave is injected from the top in the ultrasonic holographic process according to principles of the present invention.

FIG. 3 provides an alternative embodiment of introducing the reference wave from emmitter 220 a topside of the hologram surface. In this case, the waveguide structure of FIG. 2 is not used, rather the object 202 receives an object wave from transducer 200 and is directly adjacent the floor 222; how ever, the hologram surface in this embodiment may no longer be a liquid-air interface 211 as shown in FIG. 2, but instead may be a liquid-liquid interface 213.

Figure 4:
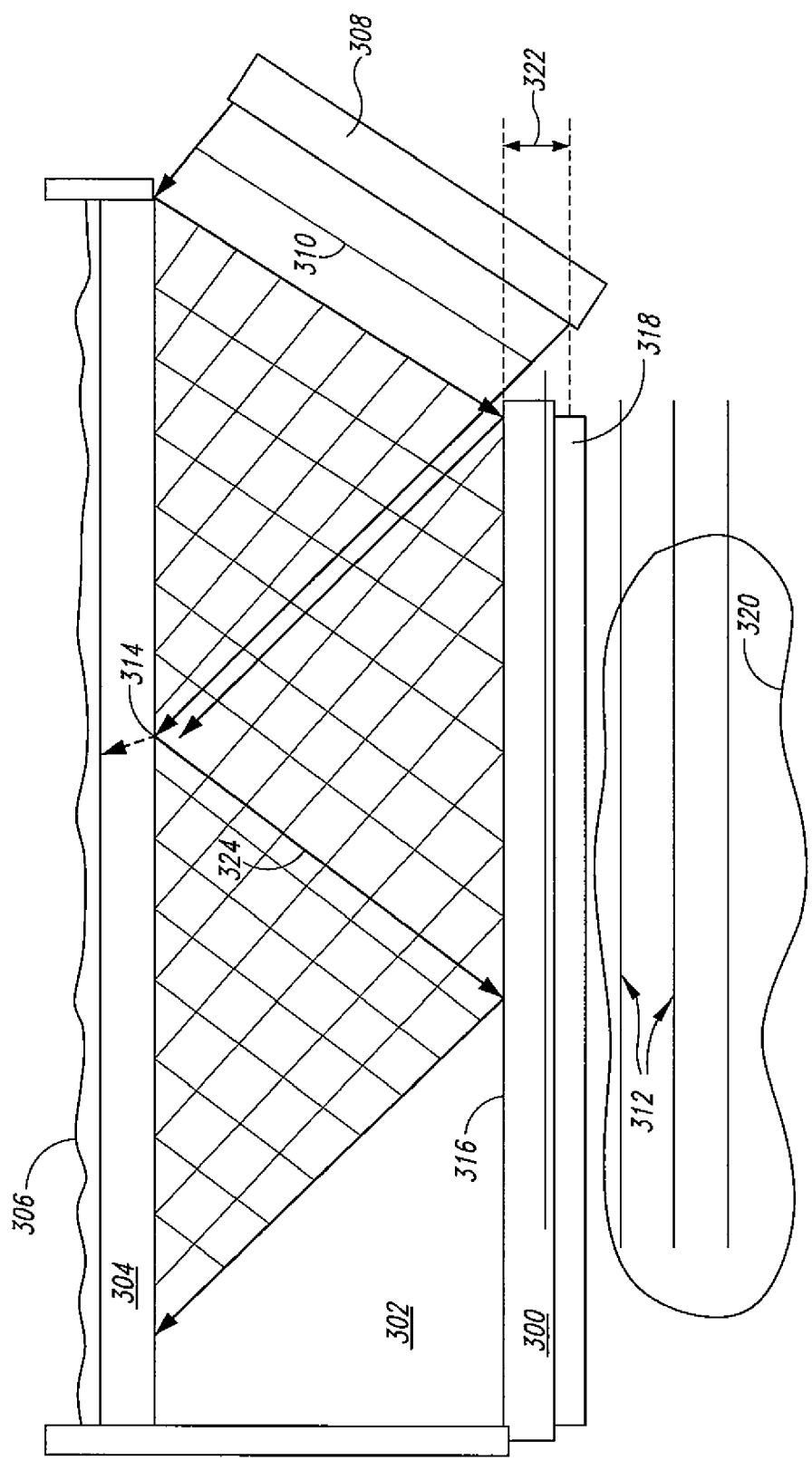
FIG. 4 is a pictographic representation of the acoustic holographic system providing further details of the reference wave pattern after the reference wave is injected from the side in the ultrasonic holographic process according to principles of the present invention.

FIG. 4 is a pictographic representation of the acoustic holographic system providing further details of the reference wave pattern after the reference wave is injected from the side in the ultrasonic holographic process according to principles of the present invention. As shown in FIG. 4, the detector floor in the prior art is replaced with a three-element acoustic waveguide assembly. This acoustical waveguide assembly includes a first solid material 300, a second solid material 304 which, in this example, is also the floor 208 or 222 and a liquid core 302 sandwiched therebetween. The acoustic object wave 312 passes through the object region 320 to penetrate the first solid material 300, the liquid core 302, the second solid material 304 and finally the detecting surface where it interferes with the reference wave 310 to form the hologram 306. According to further aspects of the invention, a bottom surface of the first solid material 300 may utilize a matching layer 318 to reduce the reflection of object wave energy upon entering the detector so that the reference wave 310 passes through a vertical distance 322 to reach the liquid core 302.

In operation, and as shown in FIG. 4, the reference wave 310 is introduced by the reference source transducer 308 at a specified angle. The wave is introduced into the liquid core 302, which is a liquid with a low acoustic attenuation, for example, such as water, alcohol, glycol, glycerin, and the like. When the wave reaches the interface between the liquid core 302 and the second solid material 304, a certain percent of the energy at position 314 will reflect from the surface and continue to propagate (as shown by arrow 324) in the liquid core 302. In the exemplary embodiment, the first solid material 300 is selected with an acoustic impedance greater than water to maximize the energy reflected at the interface 316 between the liquid core 302 and first solid material 300.

Figure 5:
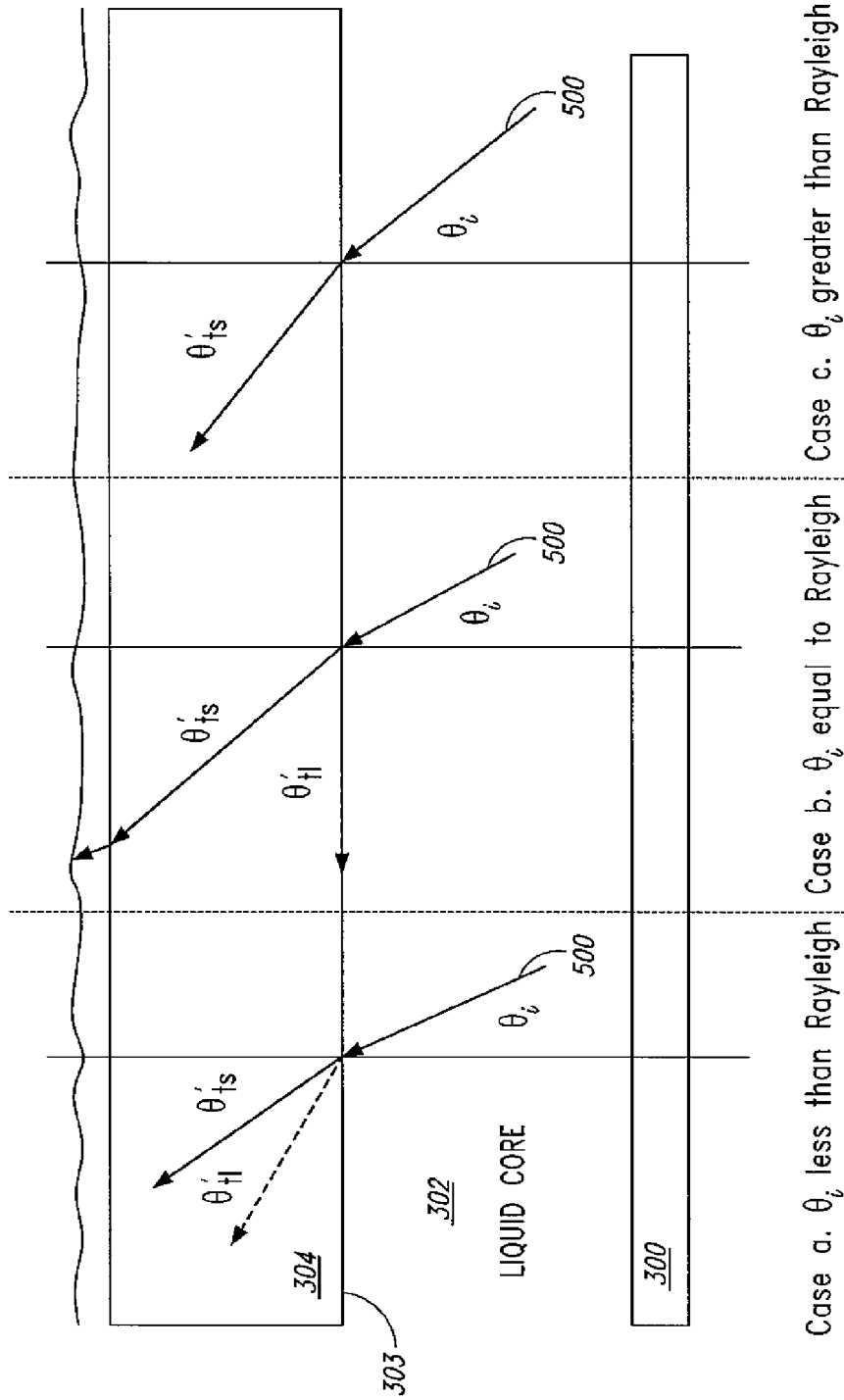
FIG. 5 is pictographic representation of a reference wave incident on the second solid material at an interface between the liquid core and the second solid material according to principles of the present invention.

The percentage of the energy from the reference wave 310 that penetrates or transmits into the second solid material 304 will be converted into a shear acoustic wave and possibly a longitudinal acoustic wave depending on the incident angle and the acoustic properties of the second solid material 304 (as shown in FIG. 5). Since the velocity of shear acoustic waves is less than that of the longitudinal acoustic waves, materials for the second solid material 304 may be selected such that the portion of the wave that is the shear acoustic wave will enter the second solid material 304, but the portion of the wave that is the faster longitudinal acoustic wave portion will be reflected since the entrance angle is beyond the Rayleigh angle. Exemplary energy 500 and the converted shear acoustic wave and longitudinal acoustic waves are shown in FIG. 5.

FIG. 5 illustrates three exemplary scenarios of converted energy from the reference wave, it is understood by those in the art that these scenarios are for exemplary purposes and that a variety of scenarios could occur. As shown in case a, the reference wave 500 introduced into the liquid core 302 at an angle of $\theta_i$ to the normal will divide into a shear wave component $\theta'_{ts}$ and a longitudinal wave component $\theta'_{tl}$ at the interface boundary 303 of the second solid material 304 and the liquid core 302. As shown in case c, if the shear wave velocity in the second solid material 304 is less than the longitudinal wave velocity in the liquid core 302, a portion of the wave will enter the second solid material 304 at a decreased angle to normal. However, as shown in case c, when the longitudinal wave velocity ($V_{L2}$) in the second solid material 304 is greater than the longitudinal velocity in the core liquid ($V_{L0}$) then there is an angle of entrance ($\theta_i$) above which all of the longitudinal wave will be reflected to remain in the liquid core 302 to again impinge on the solid material boundary after additional internal reflections. Snells law Eqn. 1 describes the minimum reference angle for shear only transmittance in the second solid material.

$$\text{Minimum angle } \theta_R \geq \sin^{-1}\left[\frac{V_{longliquid}}{V_{long2}}\sin\theta_i\right] \quad \text{Eqn. 1}$$

Where
$\theta_R$=the Rayleigh or critical angle.
$\theta_i$=the incident angle
$V_{longliquid}$=the longitudinal velocity in the liquid
$V_{long2}$=the longitudinal velocity in the second solid material According to one exemplary embodiment, if the liquid is selected to have a velocity of approximately 1497 m/sec (such as water @ 25 Degrees C.) and the second solid material is selected to have a shear velocity of 1150 m/sec and a longitudinal velocity of 2350 m/sec, for example, a plastic material such as polystyrene, then any incident angle greater $\theta_i$ than 39.6° will eliminate the undesired longitudinal wave in the second solid material. Table 1 provides the angles for cases a, b, and c shown in FIG. 5 given the stated material velocities.

TABLE 1

Incident and transmittance angles for FIG. 5

| Angle | Case a | Case b | Case c |
|---|---|---|---|
| $\theta_i$ | 20.0° | 39.6° | 80.5° |
| $\theta_{tshear}$ | 15.2° | 29.3° | 49.1° |
| $\theta_{tlong}$ | 32.4° | 90.0° | — |

Material selection also considers energy transmittance and reflectance in order to optimize propagation down the liquid core. For normally incident acoustic waves the reflection coefficient is given by Equation 2, and the transmittance coefficient is given by Equation 3. For energy reflection and transmittance, these quantities are squared. For oblique incident, these equations are much more complex and can be approximated by Equation 4, where k is a correction factor.

$$\text{Reflection coefficient } \Gamma = \frac{Z_{Solid} - Z_{liquid}}{Z_{Solid} + Z_{liquid}}. \quad \text{Equation 2}$$

Where
$Z_{solid}$=Acoustic impedance of the shear wave for the second solid material
$Z_{liquid}$=Acoustic impedance of the liquid core $$\text{Transmission Coefficient } \tau = \frac{2Z_{Solid}}{Z_{Solid} + Z_{liquid}} \quad \text{Equation 3}$$

Transmission Coefficient oblique $\tau_{approximate} \cong$      Equation 4

$$\frac{2Z_{Solid}}{Z_{Solid} + Z_{liquid}}(1 - k*\sin\theta_i).$$

| Material | Incident Angle | Approximate Energy Transmitted |
|---|---|---|
| Polystyrene | 80.5 | 65% |
| Lucite | 80.5 | 68% |
| Nylon | 80.5 | 60% |
| polyethylene | 80.5 | 20% |

Table 2 illustrates various solid materials suitable for use in exemplary embodiments; for example, table 2 shows a number of plastic materials suitable for selection as the second solid material. According to aspects of the invention, polystyrene may be selected due to its low attenuation coeffecient as compared to alternative materials.

Figure 6:
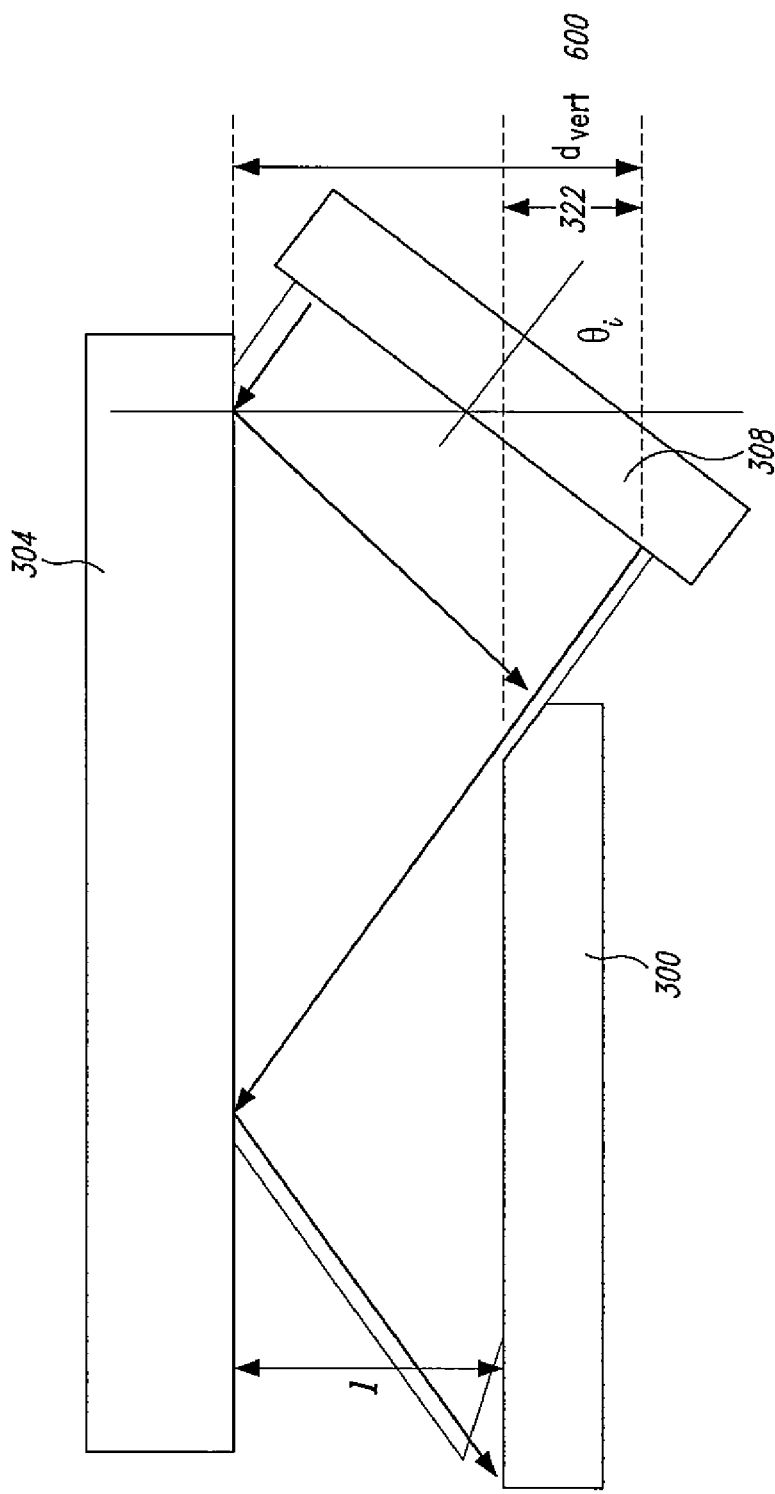
FIG. 6 is a detailed illustration of the acoustic holographic system providing further details of the detector floor in accordance with principles of the present invention.

As shown in FIG. 6, in order to assure complete coverage of the reference wave across the bottom 316 of the detector floor, a certain amount of offset is incorporated, as illustrated in FIG. 6.

A total vertical distance 600 is dependent on the reference angle and is given by Equation 5.

$$dvert = 2l\tan(90-\theta_i) \quad \text{Equation 5}$$

The distance l is set sufficiently large so as to minimize the number of traverses across the detecting surface yet sufficiently small so as to keep the object in close proximity to the detecting surface. According to aspects of the invention, this optimization may result in typical values of l on the order of 0.1 to 1 inch.

Figure 7:
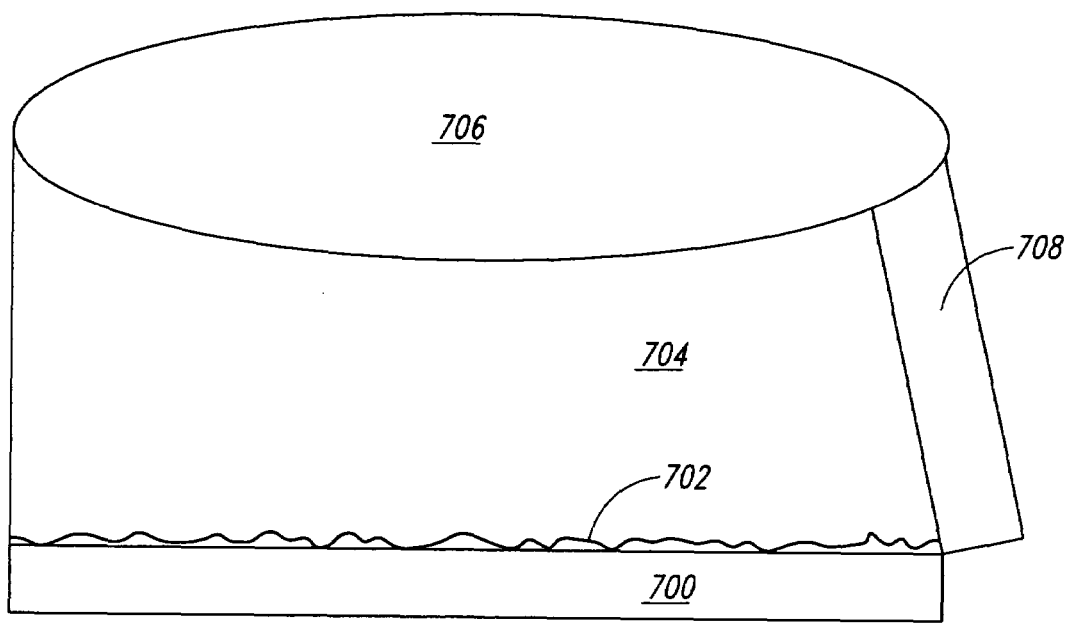
FIG. 7 is a detailed illustration of an alternate embodiment showing the reference wave introduced from the top of the detecting surface in accordance with principles of the present invention.

In an alternate embodiment, as shown in FIGS. 3 and 7, the reference wave 310 is introduced from the topside of the detecting surface. This necessitates the use of a second liquid in the volume separating the detecting surface and the optical lenses. In the exemplary embodiment, two optical transparent closure elements are illustrated as a lens.

FIG. 7 shows a detail of one exemplary embodiment showing an alternate embodiment wherein the reference wave is introduced from the top of the detecting surface in accordance with principles of the present invention. In this alternate embodiment the object wave from the emmitter 708 passes through the object, the second solid material 700 and enters the detecting region as before. However, in the alternate embodiment the detecting surface may be a liquid-liquid surface rather than a liquid-air surface as in previously disclosed embodiments. The interface between a thin fluid media 702 lying on top of the second solid material 700 and a second less dense liquid 704, resting on top of the first media 702 becomes the detecting surface. The reference wave source transducer is placed above the detecting surface at the preferred angle. The second media 704 acts as the acoustic coupling agent for the reference wave that interferes with the object at the detecting surface to form the hologram.

In this embodiment the chamber is completely filled with either a liquid or gas from the enclosure top to the second solid material. According to aspects of the invention, the enclosure top may be an optical lens 706 an optical transparent cover. Desirable aspects relevant to selecting these two fluid medias include:
    assure no mixing but complete separation
    optimize the acoustic reflection off of the detecting surface
    optimize the optical reflection off of the detecting surface
    provide for transmission of ultrasound and light through second media.

Acoustic reflection is described above and referred to in Equation 2. Table 3 gives exemplary combinations of fluids to achieve the tolerances stated above.

|  | | Media 1 | | | | | |
| --- | --- | --- | --- | --- | --- | --- | --- |
| | | Water | | FC43 | | FC77 | |
| | | | | Density | | | |
| | | 1.0 | | 1.86 | | 1.78 | |
| Media 2 | density | Acoustic Reflect | Optical Reflect | Acoustic Reflect | Optical Reflect | Acoustic Reflect | Optical Reflect |
| Air | .59 | 77.0% | 79.9% | 72.4% | 15.9% | 68.9% | 15.4% |
| Acetone | .79 | 23.4% | 32.2% | 13.3% | 53.8% | 23.4% | 54.1% |
| Water | 1.0 | 00.0% | 00.0% | 10.4% | 73.3% | 17.2% | 73.5% |
| Ethylene Glycol | 1.1 | 07.7% | 23.2% | 17.9% | 60.4% | 07.7% | 60.7% |
| Glycerin | 1.26 | 23.0% | | 32.5% | | 23.0% | |

Exemplary fluids selected for the thin layer of the first media 702 may belong to the fluorocarbon family. These fluids are especially suited for a fluid-fluid interface due to their high-density attributes and their low solubility with other fluids. Although the reflectivity is substantially reduced from the liquid-air interface, the increase in the optical reflectivity helps to compensate for the difference.

Other Considerations

Solid Waveguide

In the apparatus described in FIG. 4, a single solid material that acts as a waveguide may replace the first and the second solid materials.

Ducted Shear Wave Reference

In the case of the solid waveguide as described above, the reference transducer may be situated such that a ducted shear wave traveling parallel to the detecting surface would travel down the solid material. In this scenario the reference contribution to the hologram would be an evanescent wave that "leaks" out of the solid material into the detecting fluid.

Multiple References Sources

An alternative embodiment to both the side injected reference as well as the top injected reference shown and described with respect to FIGS. 3 and 4 respectively, would be the addition of multiple reference sources. By injecting a reference wave from opposite ends of the detecting surface, the total travel distance required for the signal strength from each is cut in half and thus the signal attenuation is dramatically reduced. According to aspects of this embodiment, the sources may be toggled so that only one reference is on for every hologram created. One objective of this embodiment is to provide a means of making the reference energy level consistent across the length of the hologram. In other words, when the reference is injected from only one side, there is attenuation as the wave progresses across the width of the hologram detector. By injecting alternate reference pulses from the opposite side, the reference energy level will remain more consistent across the hologram. Since the viewing consists of averaging the image of several separate holograms in a short time span (i.e. 1/30 of a second) the image displays the average image intensity resulting from these reference energy injected from alternate sides.

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to ultrasonic holography, not necessarily the exemplary ultrasonic holographic system generally described above.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all ultrasonic holographic systems, methods or components that operate in accordance with the claims. Accordingly, the invention is not limited by the disclosure, but instead its scope is to be determined entirely by the following claims.

We claim:

1. An apparatus comprising:
   an acoustic waveguide assembly, the acoustic waveguide assembly having a first material, a second material and a core material sandwiched therebetween; and
   a hologram detector coupled to the acoustic waveguide assembly;
   wherein the acoustic waveguide assembly includes a reference wave having a shear wave portion and a longitudinal wave portion, wherein the reference wave is converted into the shear acoustic wave portion and the longitudinal wave portion upon transmission into the second material.

2. The apparatus of claim 1 wherein acoustic waveguide assembly forms a first side of the hologram detector.

3. The apparatus of claim 1 wherein the second material is polystyrene.

4. The apparatus of claim 1 wherein the second material forms a second side of the acoustic waveguide assembly.

5. The apparatus of claim 1 wherein the core material is a liquid.

6. The apparatus of claim 1 wherein the hologram detector includes a detector floor, wherein the detector floor has an offset.

7. The apparatus of claim 1 further comprising:
multiple reference wave sources.

8. The apparatus of claim 1 wherein the hologram detector is a single solid waveguide.

9. A method of generating an acoustic hologram comprising:
coupling an object to an object transducer, wherein the object is proximate to the object transducer;
coupling a hologram detector assembly to the object wherein the object is proximate to the hologram detector assembly;
introducing an object wave from the object into a first side of the hologram detector assembly; and
introducing a reference wave from a reference transducer into a second side, different from the first side, of the hologram detector assembly to form an ultrasonic hologram.

10. The method of claim 9 wherein the hologram detector assembly includes an acoustical waveguide assembly and further comprising:
passing the reference wave through an acoustical waveguide assembly.

11. The method of claim 9 wherein the reference wave forms an ultrasonic hologram by utilizing shear wave absorption and longitudinal wave reflections to distibute the reference wave across the hologram.

12. The method of claim 9 further comprising:
introducing multiple reference waves from multiple reference wave sources.

13. The method of claim 9 wherein introducing the reference wave from the transducer to form a hologram introduces the reference wave to a topside of the hologram detector assembly.

14. An apparatus comprising:
a hologram detector;
an object acoustic transducer positioned on a first side of the hologram detector and positioned to emit object waves to pass through an object and impinge upon the hologram detector;
a reference wave transducer positioned on a second side of the hologram detector positioned to emit reference waves that impinge upon the hologram detector, the object wave and the reference wave entering the hologram detector from different sides.

15. The apparatus according to claim 14 wherein an interference pattern that is an acoustic hologram is created inside one portion of the hologram detector and pass to another portion of the hologram detector for detection.

16. The apparatus according to claim 14 wherein the hologram detector includes a waveguide assembly as a portion of the hologram detector and the object wave is introduced into the waveguide assembly from the first side of the waveguide assembly and the reference wave is introduced from a second side of the waveguide assembly.

17. The apparatus according to claim 16 wherein the first side the floor of the hologram detector and the second side is a side wall of the hologram detector.

18. The apparatus according to claim 16 wherein the reference transducer is position between a waveguide lower member and a waveguide upper member and to the side of the hologram detector.

19. The apparatus according to claim 18 where in the waveguide upper member is also the floor of a chamber holding a liquid that creates an image of the acoustic hologram.

20. The apparatus according to claim 14 wherein the reference transducer is in a side wall of the hologram detector chamber and positioned above the floor of the hologram detector and above the location in the hologram detector where a liquid creates an image of the acoustic hologram.

21. The apparatus according to claim 14 further including:
an object positioned adjacent the hologram detector.

22. The apparatus according to claim 21 in which the object is adjacent the hologram detector and is sufficiently close that there is no focusing lens system between the object and the hologram detector.

23. The apparatus according to claim 22 further including an impedance matching layer positioned between the hologram detector and the object.

* * * * *